US00PP08481P

United States Patent [19]

VandenBerg

[11] Patent Number: Plant 8,481

[45] Date of Patent: Nov. 30, 1993

[54] CHRYSANTHEMUM PLANT NAMED SOFT PASION

[75] Inventor: Cornelis P. VandenBerg, Salinas, Calif.

[73] Assignee: Yoder Brothers, Inc., Barberton, Ohio

[21] Appl. No.: 919,878

[22] Filed: Jul. 27, 1992

[51] Int. Cl.[5] ..... A01H 5/00

[52] U.S. Cl. ..... Plt./80

[58] Field of Search ..... Plt./76, 80, 81

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *C. morifolium*", Euphytica, 29:526-530.

Gosling, ed., 1979, "The Chrysanthemum Manual—6th edition", The National Chrysanthemum Society, London, Essex Telegraph Press, Ltd., pp. 329-336.

Broertjes, et al., 1978, "Application of Mutation Breeding Methods In the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

Chan, 1966, "Chrysanthemum and rose mutations induced by X∝rays", Am. Soc. Hort. Sci. Proc., pp. 613-620.

Broertjes, 1966, "Mutation breeding of Chrysanthemums", Euphytica, 15:156-162.

Dowrick et al., 1966, "The induction of mutations in Chrysanthemum using X- and gamma radiation", Euphytica, 15:204 210.

*Primary Examiner*—Howard J. Locker

*Attorney, Agent, or Firm*—Foley & Lardner

[57] ABSTRACT

A Chrysanthemum plant named Soft Pasion particularly characterized by its flat capitulum form; decorative capitulum type; soft pink ray floret color, with a darker center of the flower; diameter across face of capitulum of 73 to 76 mm when fully opened, when grown as a single stem spray cut mum; photoperiodic flowering response to short days when grown in Salinas, Calif., is 53 to 57 days after start of short days; flowering response in Bogota, Colombia is 65 to 66 days; plant height is 81 to 114 cm when grown in Salinas with 17 to 18 long days prior to start of short days; height is 114 to 137 cm when grown in Bogota with 21 long days prior to start of short days; peduncle length of the first lateral at flowering after removing the apical bud without growth regulator applications is 3 to 8 cm when grown in Salinas, and 3 to 5 cm when grown in Bogota; peduncle length of the fourth lateral at flowering is 8 to 13 cm when grown in Salinas, and 8 to 13 cm when grown in Bogota; and excellent tolerance to minimum low night temperatures of 7° C. for bud initiation and flower development.

1 Drawing Sheet

The present invention comprises a new and distinct cultivar of Chrysanthemum, botanically known as *Dendranthema grandiflora, and referred to by the cultivar name Soft Pasion.*

Soft Pasion, identified as 0626 (85-251C01), is a product of a mutation induction program. The new cultivar was discovered and selected by Cornelis P. VandenBerg on Jan. 30, 1990, in a controlled environment in Salinas, Calif., as one flowering plant within a flowering block established as rooted cuttings from stock plants which had been exposed as unrooted cuttings to an X-ray source of 2000 rads in Fort Myers, Fla., on Jun. 29, 1989. The irradiated parent cultivar was the cultivar identified as Pasion, disclosed in U.S. Plant Pat. No. 7,489. Pasion is described as a decorative spray cut mum with a flat capitulum form; a light red-purple ray floret color, with a darker red-purple center of the flower; diameter across face of capitulum of 63 to 76 mm when fully opened; flowering response period of 50 to 58 days after start of short days in Salinas, Calif., and of 63 to 70 days in Bogota, Colombia; plant height of 79 to 107 cm when grown in Salinas with 14 to 18 long days prior to start of short days, and of 117 to 130 cm when grown in Bogota with 20 to 21 long days prior to start of short days; and excellent tolerance to low night temperatures for bud initiation and flower development. The above description of Pasion has a wider range of measurements than the description of Pasion in U.S. Plant Pat. No. 7,489. This is based on the continued flowering trials of Pasion after preparing the plant patent application for Pasion. Pasion was commercially introduced in July 1990.

The irradiation program resulting in Soft Pasion had as its primary objective the expansion of color ranges of the parent cultivar Pasion. The irradiation program comprised irradiating cuttings of the parent cultivar at irradiation levels of 1500, 1750 and 2000 rads. A total of 1149 cuttings harvested from a total of 225 irradiated plants were planted on Nov. 6, 1989, Oct. 23, 1989 and Oct. 2, 1989, respectively. Of these, 13 initial selections were made, which selections were than revegetated and reflowered. Three consecutive flowerings resulted in discarding 8 of the original 13 selections on Nov. 1, 1990, while five codes (plants) were retained as PI (Possible Introduction) status. The five retained codes were further tested in Salinas, Calif., and in Bogota, Colombia, ultimately resulting in discarding two of these codes, and the decision to introduce code 0626 as Soft Pasion, code 0620 as Bronze Pasion, and code 0701 as Deep Pasion. Bronze Pasion and Deep Pasion are disclosed in pending applications of applicant.

The first act of asexual reproduction of Soft Pasion was accomplished when vegetative cuttings were taken from the original selection in Apr. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Soft Pasion are firmly fixed and are retained through successive generations of asexual reproduction.

Soft Pasion has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia.

The following traits have been repeatedly observed and are determined to be basic characteristics of Soft Pasion, which, in combination, distinguish this Chrysanthemum as a new and distinct cultivar:

1. Flat capitulum form.
2. Decorative capitulum type.
3. Soft pink ray floret color, with a darker center of the flower.
4. Diameter across face of capitulum of 73 to 76 mm when fully opened, when grown as a single stem spray cut mum.
5. Photoperiodic flowering response to short days when grown in Salinas, Calif., is 53 to 57 days after start of short days. Flowering response in Bogota, Colombia is 65 to 66 days.
6. Plant height is 81 to 114 cm when grown in Salinas with 17 to 18 long days prior to start of short days; height is 114 to 137 cm when grown in Bogota with 21 long days prior to start of short days.
7. Peduncle length of the first lateral at flowering after removing the apical bud without growth regulator applications is 3 to 8 cm when grown in Salinas, and 3 to 5 cm when grown in Begota. Peduncle length of the fourth lateral at flowering is 8 to 13 cm when grown in Salinas, and 8 to 13 cm when grown in Bogota.
8. Excellent tolerance to minimum low night temperatures of 7° C. for bud initiation and flower development.

The accompanying photographic drawing is a side view of a single stem cut spray mum of Soft Pasion, with the colors being as nearly true as possible with illustrations of this type.

Of the commercial cultivars known to the inventor, the most similar in comparison to Soft Pasion is the parent cultivar Pasion. All traits of Soft Pasion are similar to those of Pasion, except for the ray floret color, the flowering response, and the plant height. Soft Pasion has a soft pink ray floret color with a darker center of the flower, while Pasion has a light red-purple ray floret color with a darker red-purple center of the flower. In most of our flowering trials, Soft Pasion has a slower flowering response to short days of two to three days when compared with Pasion, and has 3 to 7 cm more vigor than Pasion. In a recent trial in Colombia, Soft Pasion had an average of one flower less per stem in comparison with Pasion.

In the following description color references are made to the Royal Horticultural Society Colour Chart. The color values were determined on plant material grown as a single stem spray cut mum in Salinas, Calif. on Dec. 30, 1991.

Classification:

*Bottanical.*—*Dendranthema grandiflora* cv Soft Pasion.

*Commercial.*—Flat decorative cut spray mum.

INFLORESCENCE

A. Capitulum:

*Form.*—Flat.

*Type.*—Decorative.

*Diameter across face.*—73 to 76 mm when fully opened.

B. Corolla of ray florets:

*Color (general tonality from a distance of three meters).*—Soft pink, with a darker center of the flower.

*Color (upper surface).*—49D. Inner ray florets are closest to 49B.

*Color (under surface).*—49C to 49D.

*Shape.*—Straight, oblong, slightly ribbed.

C. Corolla of disc florets:

*Color (mature).*—Closest to 12A.

*Color (immature).*—Closest to 144B.

D. Reproductive organs:

*Androecium.*—Present on disc florets only; no pollen.

*Gynoecium.*—Present on both ray and disc florets.

PLANT

A. General aappearance:

*Height.*—81 to 114 when grown in Salinas with 17 to 18 long days prior to start of short days; height is 114 to 137 cm when grown in Bogota with 21 long days prior to start of short days.

B. Foliage:

*Color (upper surface).*—147A.

*Color (under surface).*—147B.

I claim:

1. A new and distinct Chrysanthemum plant named Soft Pasion, as described and illustrated.

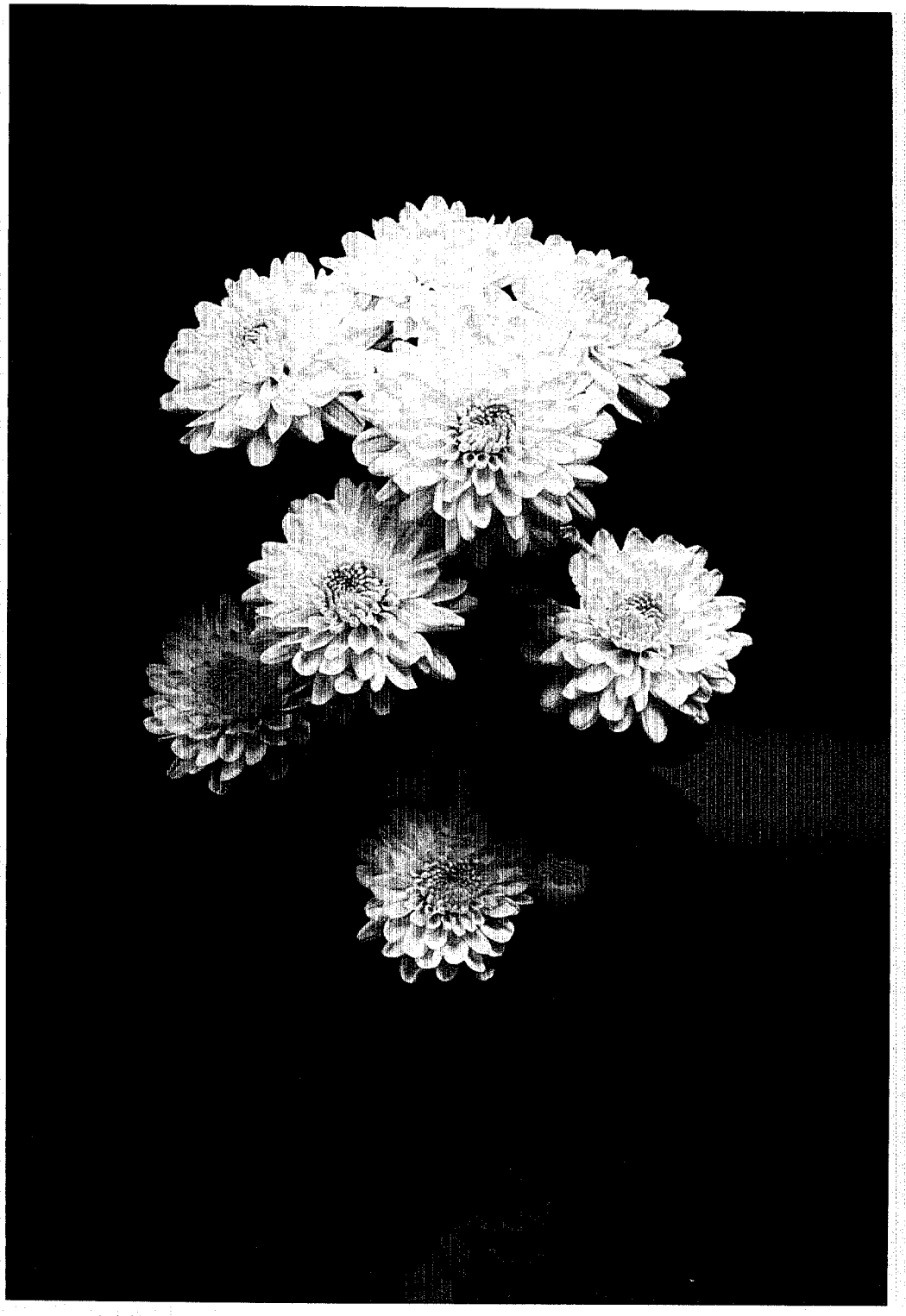

* * * * *